(12) United States Patent
Guadagno et al.

(10) Patent No.: US 9,488,666 B2
(45) Date of Patent: Nov. 8, 2016

(54) ASSAY FOR DETERMINATION OF LEVELS OF LIPOPROTEIN PARTICLES IN BODILY FLUIDS

(75) Inventors: Philip Angelo Guadagno, Mechanicsville, VA (US); Debra Linn Hicks, Orange, TX (US); Joseph Paul McConnell, Richmond, VA (US)

(73) Assignee: Helena Laboratories Corporation, Beaumont, TX (US)

( * ) Notice: Subject to any disclaimer, the term of this patent is extended or adjusted under 35 U.S.C. 154(b) by 268 days.

(21) Appl. No.: 12/877,733

(22) Filed: Sep. 8, 2010

(65) Prior Publication Data
US 2012/0052594 A1    Mar. 1, 2012

Related U.S. Application Data

(63) Continuation-in-part of application No. 12/861,829, filed on Aug. 24, 2010, now abandoned.

(51) Int. Cl.
G01N 33/566 (2006.01)
G01N 33/559 (2006.01)
G01N 27/447 (2006.01)
G01N 33/92 (2006.01)

(52) U.S. Cl.
CPC ........... *G01N 33/92* (2013.01); *G01N 2800/32* (2013.01)

(58) Field of Classification Search
None
See application file for complete search history.

(56) References Cited

U.S. PATENT DOCUMENTS

| 5,064,769 | A | * | 11/1991 | Gambert et al. ............ 436/516 |
| 5,928,484 | A | | 7/1999 | Bellon et al. |
| 7,062,077 | B1 | * | 6/2006 | Kelley ......................... 382/128 |
| 2004/0053321 | A1 | * | 3/2004 | Koren et al. ................... 435/7.1 |
| 2007/0072302 | A1 | * | 3/2007 | Clendenen et al. ............ 436/71 |
| 2012/0052593 | A1 | * | 3/2012 | Guadagno et al. ........... 436/501 |

FOREIGN PATENT DOCUMENTS

| EP | 0141001 | 5/1985 |
| JP | 2007248131 | 9/2007 |
| WO | 0060358 | 10/2000 |

OTHER PUBLICATIONS

Rainwater et al., "Distribution of specific apolipoproteins determined by immunoblotting of baboon lipoproteins resolved by polyacrylamide gradient gel electrophoresis," Biochemical Genetics, 1992, vol. 30, No. 3-4, pp. 143-158.*
Hidaka et al., "Characterization of Triglyceride Rich Lipoproteins with Very Light Density by Ultracentrifugation and Agarose Gel Electrophoresis using Triglyceride- and Cholesterol-Staining," Ann. Clin. Lab. Sci., 2003, vol. 33 No. 2, pp. 167-178.*
Contois et al., "Quantitative determination of cholesterol in lipoprotein fractions by electrophoresis," Clin. Chim. Acta, 1999, vol. 282, issues 1-2, pp. 1-14.*
Davidson, "Is LDL-C passed its prime? The emerging role of non-HDL, LDL-P, and ApoB in CHD risk assessment," Arterioscler. Thromb. Vasc. Biol. 2008, vol. 28, No. 9, pp. 1582-1583.*
Bossuyt et al., "Serum protein electrophoresis and immunofixation by a semiautomated electrophoresis system," Clin. Chem., 1998, vol. 44, No. 5, pp. 944-949.*
Guadagnoa et al., "Validation of a lipoprotein(a) particle concentration assay by quantitative lipoprotein immunofixation electrophoresis," Clin. Chim. Acta, Jan. 15, 2015, vol. 439, pp. 219-224.*
Health Diagnostics Laboratory, Inc.; HDL-210 Test Guide Utility; pp. 1-148, Feb. 28, 2010.
Dolphin, Peter J., "Two Dimensional Immunoelectrophoresis of Rat Serum Apolipoproteins", Electrophoresis, vol. 2, No. 2, Feb. 1, 1981, pp. 113-116, XP55149005, ISSN:0173-0835, DOI: 10.1002/elps.1150020208.
Fruchart, J.C., et al., "Simultaneous Measurement of Plasma Apolipoproteins A-1 and B by Electroimmunoassy," Clinical Chemistry, Jan. 1, 1982, pp. 59-62, XP55148999, United States, retrieved from Internet: URL:http://www.clinchem.org/cgi/content/abstract/28/1/59.
Holmquist, L., et al., "A Zone Immunoelectrophoresis Assay Method for Quantification of Apolipoprotein D in Human Cerebrospinal Fluid," Journal of Biochemical and Biophysical Methods, Amsterdam, N.L., vol. 33, No. 1, Jan. 1, 1996, pp. 1-08, XP002121480, ISSN: 0165-022X, DOI: 10.1016/0165-022X(95)00041-O.
Examiner's Report dated Nov. 4, 2014 for European Patent Application No. 11 785 815.9.
Aveynier E et al: "[Apolipoprotein (a) isoform size determination. Value and limits of high resolution phenotyping by agarose gel electrophoresis," Annales De Biologie Clinique, John Libbey Eurotext Ltd, Paris, FR, vol. 56, No. 1, Jan. 1, 1998, pp. 73-78.

* cited by examiner

*Primary Examiner* — Galina Yakovleva
(74) *Attorney, Agent, or Firm* — Jerold I. Schneider; Schneider Rothman Intellectual Property Law Group, PLLC

(57) ABSTRACT

An assembly, method, system, and apparatus for the assessment of the level of specific lipoprotein particles present in a bodily fluid are disclosed. The levels determined may be used to predict the risk of developing various diseases related to lipoprotein particles.

4 Claims, 7 Drawing Sheets

Plate: APO-B
Patient: 1

| Fraction | % |
|---|---|
| Lp(a)-P | 3.2 |
| VLDL-P | 32.4 |
| LDL-P | 64.4 |

Plate: APO-B
Patient: 2

| Fraction | % |
|---|---|
| ApoB Probed Component | 10.3 |
| Lp(a)-P | 18.3 |
| VLDL-P | 5.6 |
| LDL-P | 65.7 |

Plate: APO-B
Patient: 3

| Fraction | % |
|---|---|
| ApoB Probed Component | 1.6 |
| Lp(a)-P | 15.9 |
| LDL-P | 82.2 |

ASSAY FOR DETERMINATION OF LEVELS OF LIPOPROTEIN PARTICLES IN BODILY FLUIDS

CROSS REFERENCE TO RELATED APPLICATION

This application is a continuation-in-art and claims priority to pending application Ser. No. 12/861,829, filed Aug. 24, 2010, the entire contents of which are incorporated herein.

FIELD

The field is an assembly, method, system, and apparatus for determining the levels of substances in bodily fluids such as serum, plasma, synovial fluid, or ascitic fluid. Specifically, the levels determined may be used to predict the risk of developing various diseases related to lipoprotein particles.

BACKGROUND

The role of lipoprotein particles is to transport water-insoluble lipids through the bloodstream to various locations in the body. Lipoprotein particles contain proteins and lipids. A lipoprotein particle includes cholesterol, triacylglycerol (triglyceride), and phospholipids. Cholesterol and triglyceride are the two major particles found in the body. Cholesterol is a steroid metabolite that is utilized in membranes of animal cells. Triglycerides are esters that are made of glycerol and three fatty acids. Phospholipids are a major portion of cell membranes. The hydrophilic components of lipoprotein particles are found on the exterior of the lipoprotein particle. Hydrophilic components include at least portions of apolipoproteins, phospholipids, and cholesterol. The hydrophobic components are found on the interior of the lipoprotein particle and include triglycerides and cholesterol esters.

Types of lipoprotein particles include high density lipoprotein particles (HDL-P), low density lipoprotein particles (LDL-P), intermediate density lipoprotein particles (IDL-P), very low density lipoprotein particles (VLDL-P), chylomicron particles (CM-P), and lipoprotein(a) particles (Lp(a)-P). Hydrolyzed VLDL-P are called intermediate density lipoproteins (IDL-P). Each varies in size, density, protein, and lipid composition.

Classes and subclasses of apolipoproteins are apolipoprotein A (Apo A-I, Apo A-II, Apo A-IV, and Apo A-V), apolipoprotein B (Apo B-48 and Apo B-100), apolipoprotein C (Apo C-I, Apo C-II, Apo C-III, and Apo C-IV), apolipoprotein D, apolipoprotein E (Apo E-2, E-3, and E-4), and apolipoprotein H.

Different lipoprotein particles have different apolipoproteins on the surface. Apolipoproteins present in HDL-P are Apo A-I, A-II, A-IV, A-V, C-I, C-II, D, E-2, E-3, and E-4. The apolipoprotein in LDL-P is Apo B-100. Apolipoproteins in IDL-P are Apo B-100, C, E-2, E-3, and E-4. Apolipoproteins in VLDL-P are Apo A-V, B-100, C-I, C-II, C-IV, E-2, E-3, and E-4. Apolipoproteins in chylomicrons are Apo A-I, A-II, A-IV, B-48, C-I, C-II, C-III, and E-2, E-3, and E-4.

A lipoprotein(a) particle (Lp(a)-P) is an LDL-like particle with apolipoprotein A bound to apolipoprotein B by a disulfide bond. Lp(a)-P is comprised of Apo B on the surface of the LDL-like particle. Higher levels of Lp(a)-P are linked to increased risk for coronary heart disease.

Separating lipoprotein particles in bodily fluids such as serum, plasma, synovial fluid, or ascitic fluid provides information on the levels of various lipoprotein particles. Various disease states are linked to levels of apolipoproteins and/or lipoprotein particles including but not limited to cardiovascular disease, Alzheimer's disease, hyperlipidemia, abetalipoproteinemia, hypothyroidism, liver disease, diabetes mellitus, and renal problems. Higher levels of apolipoprotein B and LDL particles have been associated with increased risk of cardiovascular disease. It has been disclosed that differences in the amount of cholesterol in a particle may also play a role in the risk of cardiovascular disease: Small dense LDL-P, having more cholesterol ester, appears to be correlated with a higher risk of cardiovascular disease. However, increased levels of HDL-P correlate with a decrease in risk for cardiovascular disease.

Assay of a single type of lipoprotein particle may not be sufficient to accurately determine whether an individual is at risk for a disease because determining the total amount of a lipoprotein or apolipoprotein does not indicate with which components it is associated. For example, a particular apolipoprotein bound to a particular lipoprotein may not be indicative of a risk for developing a disease whereas the same apolipoprotein bound to a different lipoprotein indicates that the individual is at risk for that disease.

Therefore, the measurement of levels of various lipoprotein particles in bodily fluids such as serum, plasma, synovial fluid, or ascites using the combination of immunological detection and lipoprotein separation simultaneously on the same matrix indicates the risk for various disease states. Accurate predictors of the risk of an individual of developing various diseases related to lipoprotein particles are needed for research, diagnostic, and therapeutic purposes.

SUMMARY

An embodiment is an assembly for assessment of the level of specific lipoprotein particles present in a bodily fluid comprising: a substrate to receive a bodily fluid sample; an antibody to detect an immunologically active agent associated with lipoprotein particles or components of lipoprotein particles; a reagent applied to the substrate for detection of the presence of proteins or lipids; and whereas a signal indicates the presence of specific lipoprotein particles. An embodiment, further comprising a device for detecting a signal used to quantitate the level of said specific lipoprotein particles. In an embodiment, said substrate is a gel for gel electrophoresis. In an embodiment, the immunologically active agent detected is selected from the group consisting of apolipoprotein A, apolipoprotein B, apolipoprotein C, apolipoprotein D, apolipoprotein E, apolipoprotein H, lipoprotein (a), high density lipoprotein, intermediate density lipoprotein, low density lipoprotein, very low density lipoprotein, and mixtures thereof. In an embodiment, said assembly further comprises a processor to quantitate the level of lipoprotein particles. In an embodiment, an elevated level of apolipoprotein B and low density lipoprotein particles signifies that an individual has increased risk for cardiovascular disease. In another embodiment, an elevated level of apolipoprotein B and lipoprotein (a) particles signifies that an individual has increased risk for cardiovascular disease. In another embodiment, an elevated level of apolipoprotein B and low density lipoprotein particles and lipoprotein(a) particles signifies that an individual has increased risk for cardiovascular disease.

An embodiment is a method of assessing the level of specific lipoprotein particles present in a bodily fluid comprising: separating lipoprotein particles present in a bodily fluid sample on a substrate; exposing the substrate to an antibody to detect an immunologically active agent associated with lipoprotein particles or components of lipoprotein particles; exposing the substrate to a reagent for detection of the presence of proteins or lipids; determining the level of specific lipoprotein particles. In an embodiment, separating occurs by gel electrophoresis and the substrate is a gel. An embodiment further comprises determining an optical density of a signal on the substrate indicating the level of a specific lipoprotein particle. Another embodiment further comprises visually detecting a signal on the substrate indicating the level of a specific lipoprotein particle. In an embodiment, the immunologically active agent is selected from the group consisting of apolipoprotein A, apolipoprotein B, apolipoprotein C, apolipoprotein D, apolipoprotein E, apolipoprotein H, lipoprotein (a), high density lipoprotein, intermediate density lipoprotein, low density lipoprotein, very low density lipoprotein, and mixtures thereof. In an embodiment, the component is apolipoprotein B.

An embodiment is a system for assessment of the level of specific lipoprotein particles present in a bodily fluid comprising: a separation apparatus to separate lipoprotein particles present in a bodily fluid sample; an antibody to detect an immunologically active agent associated with lipoprotein particles or components of lipoprotein particles; and a reagent applied to the substrate for detection of the presence of lipoprotein particles. In an embodiment, the separation apparatus is an electrophoretic apparatus. In an embodiment, an electrophoretic pattern of the bodily fluid sample is detected visually. An embodiment further comprises a densitometer for determining optical density of an electrophoretic pattern of the bodily fluid sample for assessment of the level of specific lipoprotein particles. An embodiment further comprising a processor to quantitate the level of lipoprotein particles. In an embodiment, the immunologically active agent is selected from the group consisting of apolipoprotein A, apolipoprotein B; apolipoprotein C; apolipoprotein D; apolipoprotein E; apolipoprotein H; lipoprotein (a), high density lipoprotein, intermediate density lipoprotein, low density lipoprotein, very low density lipoprotein, and mixtures thereof. In an embodiment, the component is apolipoprotein B.

An embodiment is an apparatus for assessment of the level of specific lipoprotein particles present in a bodily fluid comprising: a separation apparatus to separate lipoprotein particles present in a bodily fluid sample on a gel; a densitometer for determining the optical density of an electrophoretic pattern of the bodily fluid sample for assessment of the level of specific lipoprotein particles; and a processor for correlating the level of said optical density of the electrophoretic pattern of the bodily fluid sample for assessment of the level of specific lipoprotein particles. In an embodiment, the separation apparatus is an electrophoretic apparatus.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 4 illustrates two bands in the area of where Lp(a)-P migrates, one of which co-migrates with HDL-P. (Fraction Labels: Lp(a)-P1, Lp(a)-P2, VLDL-P, LDL-P)

DETAILED DESCRIPTION

Figure 1:
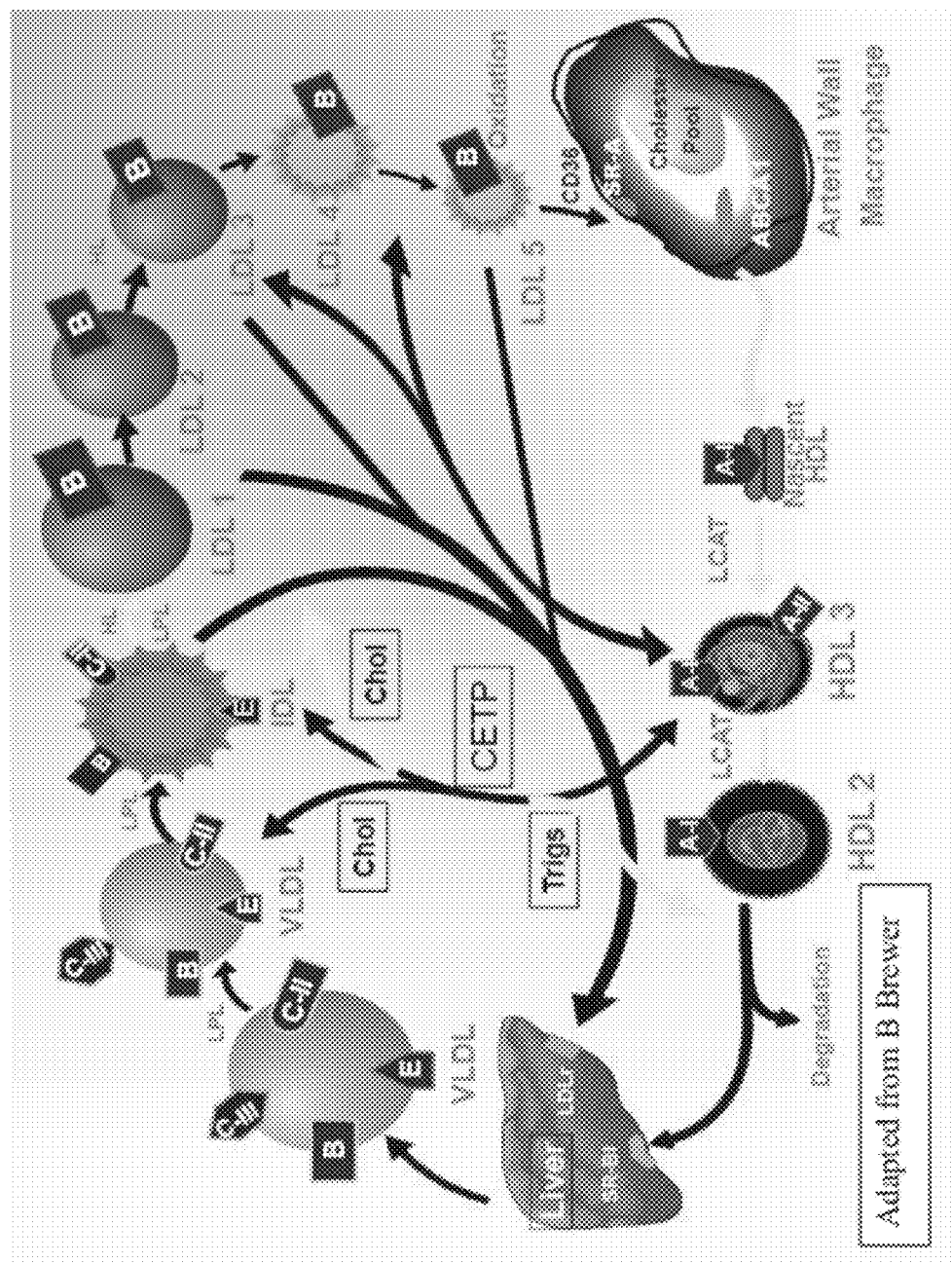
FIG. 1 depicts a diagram of lipoprotein particle metabolism.

The disclosure relates to an assembly, method, system, and apparatus for the integrated determination of levels of apolipoproteins, lipoprotein particles, proteins, and lipids in bodily fluids such as serum, plasma, synovial fluid, and ascitic fluid as an indicator of lipoprotein particle number. These levels may be used as predictors of the risk of developing various diseases related to lipoprotein particle number. In addition, numerous specific details are set forth in order to provide a thorough understanding of the example embodiments described herein. However, it will be understood by those of ordinary skill in the art that the example embodiments described herein may be practiced without these specific details. In other instances, methods, procedures and components have not been described in detail so as not to obscure the embodiments described herein.

The following definitions and explanations are meant and intended to be controlling in any future construction unless clearly and unambiguously modified in the following Description or when application of the meaning renders any construction meaningless or essentially meaningless. In cases where the construction of the term would render it meaningless or essentially meaningless, the definition should be taken from Webster's Dictionary, 3rd Edition. Definitions and/or interpretations should not be incorporated from other patent applications, patents, or publications, related or not, unless specifically stated in this specification or if the incorporation is necessary for maintaining validity.

The term "lipoprotein particle", as used herein, refers to a particle that contains both protein and lipid.

The term "lipoprotein particle number", refers to the number of the lipoprotein particles present in the bodily fluid.

The term "apolipoprotein", as used herein, refers to a protein that combines with lipids to form a lipoprotein particle. The unique nature of the apolipoprotein is their stoichiometric relationship to lipoprotein particles, providing an estimate of the lipoprotein particle number.

The term "lipoprotein(a) particle" also referred to as lipoprotein little 'a' and designated (Lp(a)-P), as used herein, refers to an LDL-like particle with apolipoprotein A bound to apolipoprotein B by a disulfide bond.

The terms cardiovascular disease (CVD), coronary artery disease (CAD), and coronary heart disease (CHD) are used interchangeably herein.

An assembly, method, apparatus, and system for separating and assaying lipoprotein particles and apolipoproteins are disclosed. The assembly, method, apparatus, and system are used to determine which individuals are at a higher risk for a given disease state by the level of lipoprotein particles comprised of various lipoprotein particles and apolipoproteins. The presence of cholesterol, phospholipids and triglycerides as part of a given lipoprotein particle is also detectable.

An assembly, method, apparatus, and system are disclosed that allow simultaneous, modifiable, charge/size lipoprotein particle separations to be probed immunologically for various apolipoprotein. The assembly, method, apparatus, and system provide an improved method for direct measurement of lipoprotein particles. Elevated levels of Apo B, Lp(a)-P and LDL-P particles are known to correlate to increase risk of cardiovascular disease.

There are many variations that may enhance separation and detection. However, the combination electrophoretic separation and immunological detection offers heretofore unavailable clinical information for disease; including cardiovascular disease, risk assessment.

An advantage of the present systems, methods, assemblies, and apparatus are that lipoprotein particle separation and integrated detection of components and immuno-recognition are available on the same gel simultaneously, providing the ability to distinguish what amount of which apolipoproteins or other components including but not limited to triglycerides, phospholipids, and cholesterol are bound to what amounts of certain lipoprotein particles. It is beneficial to not have to use multiple gels, multiple instruments, and/or multiple methods to detect this information. The reasons for detecting this information simultaneously are that a bias occurs when gels, multiple instruments, and/or multiple methods are used. Simultaneous detection eliminates this source of variability.

Lipid Metabolism

Fatty acids, cholesterol, monoacylglycerols, and bile acids are absorbed in the intestine. Bile acids are found in intestinal bile and aid in the digestion of fats by the formation of micelles to emulsify the fats. Bile acids are stored in the gallbladder until they are secreted into the intestine after eating. Intestinal epithelial cells synthesize triacylglycerols. A portion of the cholesterol is esterified to form cholesterol esters. Intestinal cells form chylomicrons from triacylglycerols, cholesterol esters, phospholipids, free cholesterol; and apolipoproteins.

Apolipoproteins

Apolipoproteins are the protein component of lipoprotein particles. Apolipoproteins coat lipoprotein particles that include cholesterol esters and triacylglyceride. The coat of the lipoprotein particle is made up of unesterified cholesterol, phospholipids, and apolipoproteins. The unique nature of the apolipoprotein is their stoichiometric relationship to lipoprotein particles, providing an estimate of the lipoprotein particle number. These lipoprotein particles provide a way to circulate the hydrophobic components throughout the bloodstream. Different lipoprotein particles include chylomicron-P, VLDL-P, IDL-P, LDL-P, and HDL-P. Lipoprotein particles vary in size, density, apolipoprotein composition, and lipid composition. There is heterogeneity within each class with each class sharing similar physical characteristics. By varying conditions, it is possible visualize different particles within a class. There is clinical merit in doing so because, for example, one class may be atherogenic and one class may be atheroprotective. FIG. 1 illustrates a diagram of lipoprotein particle metabolism.

The apolipoprotein A (Apo A) family constitute the major proteins found in HDL-P and triglyceride-rich lipoprotein particles. Apo A, as part of HDL-P, is involved in the removal of free cholesterol from extrahepatic tissues and also plays a role in the activation of lecithin acyltransferase. Apolipoprotein A activates the enzymes driving cholesterol transfer from the tissues into HDL-P and is also involved in HDL-P recognition and receptors binding in the liver.

There are multiple forms of apolipoprotein A. The most common forms are Apo A-I and Apo A-II. Apolipoprotein A (A-I, A-II, and A-IV) are found in chylomicrons and HDL-P. Apo A-I is the major apolipoprotein A attached to HDL-P. Apo A-I is responsible for activating lecithin-cholesterol acyltransferase and Apo A-II modulates that activation. Lecithin-cholesterol acyltransferase converts free cholesterol into a cholesterol ester. Apo A-IV secretions increase when fat is absorbed in the intestines. Apo A-IV may also function in activation of lecithin-cholesterol acyltransferase.

Apo A-I is found in greater proportion than Apo A-II (about 3 to 1). Lower levels of Apo A commonly correlate with the presence of cardiovascular disease (CVD) and peripheral vascular disease. Apo A-I may be a better predictor of atherogenic risk than HDL-cholesterol (HDL-C). Certain genetic disorders cause Apo A-I deficiencies and associated low levels of HDL particles. These patients also tend to have hyperlipidemia with elevated LDL particles. This contributes to accelerated rates of atherosclerosis. Apo A levels may be extremely low in analphalipoproteinemia (also known as familial high density lipoprotein deficiency).

The role of HDL and its major apolipoprotein Apo A-I in cholesterol efflux from macrophages has been studied extensively. While HDL-P competes for Apo A-I binding, Apo A-I is not a competitor for HDL-P binding. This observation suggests that HDL-P and Apo A-I are binding to macrophages at least in part by distinct receptors. For example, pre-β-HDL-P and lipid-free Apo A-I are poor ligands for the scavenger receptor (SR-BI), explaining the lack of competition of HDL-P binding by Apo A-I. Conversely, it has been shown that Apo A-I can dissociate from HDL-P, so that lipid-free Apo A-I could be available for the competition of the Apo A-I binding site by HDL. Lorenzi I, et al., BIJ Mol Med. 2008; 86:171-183. Apo A-II, another component of HDL, has been shown to be pro-atherogenic in animal models. Meyers C D and Kashyap M L., Curr Opin Cardiol. 2004; 19(4):366-373.

Apolipoprotein B (Apo B-100 and Apo B-48) is the protein component of LDL-P. One molecule of Apo B is present in the phospholipid layer of each LDL-P. Over 90% of the LDL particle is composed of Apo B. Apo B functions to solubilize cholesterol within the LDL-P complex, which in turn increases the transport capacity of LDL-P for subsequent deposit of LDL-P cholesterol on the arterial wall. The deposit contributes to cardiovascular disease. Apo B is also a protein component of chylomicrons, VLDL-P, IDL-P, and Lp(a)-P. Apo B is a large amphipathic helical glycoprotein with 2 isoforms: Apo B-100 (synthesized in the hepatocytes) and Apo B-48 (the structural protein of chylomicrons). Chylomicrons contain Apo B-48 while other lipoprotein particles that contain Apo B contain Apo B-100.

Apo B modulates the activity of enzymes that act on lipoprotein particles, maintains the structural integrity of the lipoprotein particle complex, and facilitates the uptake of lipoprotein particles by acting as ligands for specific cell-surface receptors. Enzymes that act on lipoprotein particles include but are not limited to lipoprotein lipase, lecithin-cholesterol acyltransferease, hepatic-triglyceride lipase, and cholesterol ester transfer protein. Elevated levels of Apo B are found in hyperlipoproteinemia. Apo B-100 is absent in forms of abetalipoproteinemia. High levels of Apo B-100 may be present in hyperlipoproteinemia, acute angina, and myocardial infarction. Apo B-48 stays in the intestine in chylomicron retention disease.

It is well established that increased plasma concentration of Apo B-containing lipoprotein particles is associated with an increased risk of developing atherosclerotic disease. Case control studies have found plasma Apo B concentrations to be more discriminating than other plasma lipids and lipoprotein particles in identifying patients with coronary heart disease (CHD). Walldius G, et al., Eur Heart J. 2003; 24: 1601-10; Walldius G and Jungner I. J Intern Med. 2004; 255/2: 188-205; Walldius G, et al., J Intern Med. 2006; 259-66; Yusuf S, et al. Lancet. 2004; 364: 937-52. The utility of Apo B in determining CHD risk has been confirmed by prospective studies, although the extent to which Apo B concentrations were better than serum lipids in predicting risk was variable. Apo B is a component of all atherogenic or potentially atherogenic particles, including very low density lipoprotein particles (VLDL-P), intermediate density lipoprotein particles (IDL-P), low density lipoprotein particles (LDL-P), and lipoprotein(a) particles(Lp(a)-P), and each particle contains one molecule of Apo B. An individual's risk to develop CVD is proportional to the individual's lipoprotein particle distribution and type. However, atherogenic Apo-B containing lipoprotein particles are differentially atherogenic. Although Apo B provides a direct measure of the number of atherogenic lipoprotein particles in the circulation, optimum clinical merit is achieved only when Apo-B measurements are used to quantitate the distribution and type of lipoprotein particles present. CVD risk assessment relative to Total Apo B will be influenced by its presence in the various particles above. Measuring total Apo B alone without separating the particles does not indicate with which particle it is associated.

There is now a clear consensus that Apo B is more strongly predictive of cardiovascular disease (CVD) than low density lipoprotein cholesterol (LDL-C) and a recent consensus conference report from the American Diabetes Association (ADA) and the American College of Cardiology (ACC) recognizes the importance of measurement of Apo B. Kannel W B, et al., Ann Intern Med 1979; 90:85-91 and Jeyarajah, E J, et al., Clin Lab Med 2006; 26: 847-70. In an embodiment, an elevated level of Apo B and LDL-P signifies that an individual has increased risk for cardiovascular disease. In an embodiment, an elevated level of Apo B, LDL-P and Lp(a)-P signifies that an individual has increased risk for cardiovascular disease.

Apolipoprotein C (Apo C-I, C-II, C-III) is a component of chylomicron particles, VLDL particles, IDL particles, and HDL particles. Apo C-II is an activator of lipoprotein lipase and a deficiency results in an accumulation of chylomicrons and triacylglycerols. High levels of Apo C-II are indicators of angina and myocardial infarction. Apolipoprotein C-II (Apo C-II) is a specific type of protein found in large particles absorbed from the gastrointestinal tract. It is also found in very low density lipoprotein particles (VLDL-P) which is made up of mostly cholesterol. Apo C-II is an apolipoprotein responsible for the activation of lipoprotein lipase (LPL) in capillaries and thus begins the catabolism of the chylomicron particles and VLDL-P. It is also found in HDL-P. Deficits of this Apo C-II present with grave hypertriglyceridemia and hyperchylomicronemia during fasting.

Apo C-II measurements can help to determine the specific type or cause of high blood lipids (hyperlipidemia). Persons with familial lipoprotein lipase deficiency may have high amounts of Apo C-II. Other disorders that may be associated with high Apo C-II levels include angina pectoris and heart attack. Low Apo levels are seen in persons with a rare condition called familial Apo C-II deficiency.

Apolipoprotein C-III (Apo C-III) is found in very low density lipoprotein particles (VLDL-P). Apo C-III inhibits lipoprotein lipase and hepatic lipase and it is thought to inhibit hepatic uptake of triglyceride-rich particles. Apo C-IV is found in at least VLDL-P and HDL-P.

The Apo A-I, Apo C-III and Apo A-IV genes are closely linked in both rat and human genomes. The A-I and A-IV genes are transcribed from the same strand, while the A-I and C-III genes are convergently transcribed. An increase in Apo C-III levels induces the development of hypertriglyceridemia.

Apolipoprotein D is a minor component of HDL-P. High concentrations of Apo D are correlated with various diseases such as gross cystic disease of the breast and Alzheimer's disease.

Apolipoprotein E (Apo E-2, E-3, and E-4) are found in chylomicrons and IDL-P. Apo E binds to a receptor on liver cells and peripheral cells. Apo E is essential for the normal catabolism of triglyceride-rich lipoprotein particle constituents. Apo E was initially recognized for its importance in lipoprotein particle metabolism and cardiovascular disease. It plays a role in the transport of lipids to the tissues, the transport of cholesterol from the organs to the liver, in lipoprotein particle metabolism by clearing VLDL-P and chylomicrons, and in formation of atherosclerotic lesions. The Apo E portion of the lipoprotein particles mediates the binding of Apo E lipoprotein particles to the LDL-P receptor. Apo E bound to HDL-P inhibits agonist induced platelet aggregation by binding to sites on the platelets. Three different alleles of the Apo E gene exist, Apo E e2, e3, and e4. Apo E e4 is associated with an increased risk of late onset Alzheimer's disease.

Apolipoprotein H functions to bind cardiolipin. Anti-cardiolipin antibodies are found in syphilis, sclerosis, and lupus and in some diseases the antibodies require Apo H to be active and inhibit serotonin release by the platelets and prevent aggregation of platelets. Apo H also inhibits serotonin release by platelets and prevents aggregation of platelets.

Lipoprotein Particles

Lipoprotein particle profiles are different for different individuals and for the same individual at different times. Chylomicrons are produced in the intestine and transport digested fat to the tissues. Lipoprotein lipase hydrolyzes triacylgylcerol to form fatty acids. Chylomicrons are one of the largest buoyant particles. VLDL-P is formed from free fatty acids upon metabolism of chylomicrons in the liver. Lipoprotein lipase hydrolyzes triacylgylcerol to form fatty acids. IDL-P is the unhydrolyzed triacylgylcerol of VLDL-P. IDL-P becomes LDL-P due to hepatic lipase. HDL-P plays a role in the transfer of cholesterol to the liver from peripheral tissues. HDL-P is synthesized in the liver and intestines.

LDL particles bind to LDL-P receptors. Upon receptor binding, LDL-P is removed from the blood. Cells use cholesterol within the LDL-P for membranes and hormone synthesis. LDL-P deposits LDL cholesterol on the arterial wall which contributes to cardiovascular disease. FIG. 1. LDL-P causes inflammation when it builds up inside an artery wall. Macrophages are attracted to the inflammation and turn into foam cells when they take up LDL-P, causing further inflammation. Smaller, denser LDL-P contain more cholesterol ester than the larger, buoyant LDL-P.

The structure of the lipoprotein(a) particles (Lp(a)-P) is that of an LDL-like particle with apolipoprotein A bound to apolipoprotein B by a disulfide bond. Lipoprotein(a) particles appear to play a role in coagulation and may stimulate immune cells to deposit cholesterol on arterial walls. An antibody to apolipoprotein B recognizes two bands in the area of where Lp(a)-P migrates. One band previously co-migrated with HDL-P and was detected using the method of simultaneous lipoprotein particle separation and immunological detection as disclosed herein. Migration differences may be associated with charge/size differentiation of isoforms of Lp(a)-P. A high lipoprotein(a)-P level indicates a higher risk for cardiovascular disease. Specifically, a high level for the slower migrating, more cathodic, band of the two is an indicator of high risk for cardiovascular disease. Therefore, Lp(a)-P is useful in diagnostic and statistical risk assessment. Lp(a)-P may serve to facilitate LDL-P plaque deposition. Levels of Lp(a)-P are increased in atherogenic events. The anodic Lp(a)-P was previously unrecognized.

Lp(a)-P may have a link between thrombosis and atherosclerosis, interfering with plasminogen function in the fibrinolytic cascade. Numerous studies have documented the relationship of high plasma Lp(a)-P concentrations to a variety of cardiovascular disorders, including peripheral vascular disease, cerebrovascular disease, and premature coronary disease. One large study of older Americans, in particular, demonstrated elevated levels of Lp(a)-P independently predict an increased risk of stroke, death from vascular disease, and death from all causes in men. Fried L P, et al. Ann Epidemiol 1991; 3:263-76.

Low-density lipoprotein cholesterol, (LDL-C), has been used for measurement for assessing cardiovascular risk. However, due to the variability of HDL-C, Apo B is a better measure of circulating LDL particle number (LDL-P) and therefore a more reliable indicator of risk than that traditional LDL-C because there is 1:1 stoichiometry of Apo B and LDL particles. The sum of total Apo B includes but is not limited to the Apo B complement of LDL-P (large buoyant particles and small dense particles), +VLDL+IDL+Lp(a)+chylomicrons. Measurement of Apo B levels as a quantitative indicator of lipoprotein particles provides additional information on the risk of atherosclerotic heart disease beyond that of the individual measurements or the traditional LDL-C assays. Measurement of fasting plasma insulin levels and LDL particle size also provide useful information.

Assays for Lipoprotein Particles and Apolipoproteins

The present systems, methods, apparatus, and assemblies may be used to determine correlations of levels of components of bodily fluids such as serum, plasma, synovial fluid, and ascitic fluid that are indicators of risk of developing a particular disease. Once a correlation is identified, a diagnostic test will be designed to provide an efficient and cost effective method of determining the risk of developing a disease, diagnosing a disease, or monitoring treatment of a disease. The diagnostic test may utilize methods including but not limited to enzyme-linked immunosorbent assay (ELISA) or other method known in the art.

In an embodiment, an elevated level of Apo B and LDL-P signifies that an individual has increased risk for cardiovascular disease. In an embodiment, an elevated level of Apo B and Lp(a)-P signifies that an individual has increased risk for cardiovascular disease. The present systems, methods, apparatus, and assemblies allow determination of the atherogenicity of Apo B and LDL-P or Apo B and Lp(a)-P. The present systems, methods, apparatus, and assemblies provide the ability to separate out various fractions, such as those for Lp(a)-P.

In one embodiment, polyclonal antibodies to an apolipoprotein are created by injecting a purified apolipoprotein and an adjuvant into a rabbit or similar host animal. Additional immunizations may be done periodically. Blood is collected periodically to determine the titer of the antibody. Antibodies are purified from the blood by allowing the blood to clot and decanting off the serum. Alternatively, antibodies may be purchased from a commercial source or produced by any other method know to one of skill in the art.

In one embodiment, electrophoresis may be utilized to separate lipoprotein particles to determine the relative levels of lipoprotein particles and apolipoproteins. During electrophoresis, an electrical field is applied to a matrix (cross-linked polymer). The matrix or medium may be polyacrylamide, agarose, cellulose-acetate, or other suitable conductive matrixed substances.

In an embodiment, the gel electrophoresis may be one-dimensional. In another embodiment, the gel electrophoresis may be two-dimensional. In an embodiment, isoelectric focusing may be performed. In an embodiment, the gel electrophoresis will use agarose or polyacrylamide. SDS-PAGE (polyacrylamide) gels separate proteins based on their size because the SDS coats the proteins with a negative charge. Separation of proteins on the agarose gel is by charge. In an embodiment, any suitable type of electrophoresis known in the art may be used.

In an embodiment, cellulose-acetate electrophoresis may be performed: Cellulose-acetate electrophoresis separates proteins based upon their charge. After separation of the lipoprotein particles by electrophoresis, the matrix may be stained to detect lipids using a lipid stain such as Fat Red 7B, Sudan Black B, Luxol fast blue, or osmium tetroxide. Cholesterol may be visualized by using an enzymatic reagent. Amido black 10B may be used to stain serum proteins. In another embodiment, particular lipoprotein particles may be detected by other methods than a stain. In certain embodiments, an antibody or other substance specific for the lipoprotein particle of interest may be used. Cholesterol: may be developed using any reagent in the art known to detect cholesterol. In an embodiment, formazan is used to detect cholesterol.

In an embodiment, the separated lipoprotein particles on the gel may be transferred to a membrane such as nitrocellulose and exposed to the desired method of detection. Gels or membranes may be exposed to stain or antibody by incubation in a wash containing the reagent, exposing the gel or membrane to a film containing the reagent, or other method known in the art. In an embodiment, films containing the reagent or reagents should be clear, rapidly dissolving, supported, and complementary to the sensitivity required for the system. Different reagents may be present on the film at different locations corresponding to a particular lane on a gel to be probed. In one embodiment, the membrane is probed with the antibody to the lipoprotein particle followed by detection with a labeled secondary antibody. The secondary antibody may be radio- or enzymatically-labeled. The optical density of each band may be determined by densitometry. In an embodiment, a processor may be used to correlate the optical densities.

Gels of varying sizes may be run containing various numbers of lanes. The serum (or other bodily fluid such as plasma, synovial fluid, or ascites) for one individual may be probed to identify multiple components and/or serum from multiple individuals may be tested. In an embodiment, the protocols for running different sizes of gels will be similar except for modifications that may be performed to optimize separation on that size of gel.

In one embodiment, immunofixation may be used to detect the amount of a given apolipoprotein associated with a given lipoprotein particle therefore providing the lipoprotein particle number due to the 1:1 stoichiometric relationship. In one embodiment, the antigen (apolipoprotein within the lipoprotein particle) is separated on the gel. In agarose gel electrophoresis, the lipoprotein migrates based upon its size and charge. Given appropriate circumstances, the binding of the antigen and the antibody causes the complex to precipitate out of the gel.

In another embodiment, the antibody is attached to a support. A fluid to be assayed, containing the antigen bound lipoprotein, may be added to the support. The binding of the antigen to the antibody allows determination of the amount of a given apolipoprotein associated with a given lipoprotein particle therefore providing the lipoprotein particle number.

In one embodiment, determination of the levels of substances in bodily fluids such as serum, plasma, synovial fluid, and ascitic fluid is used as a diagnostic assay that detects specific targets associated with certain diseases. In other embodiments, the diagnostic assay detects numerous lipoprotein particles, apolipoproteins, and other substances present in bodily fluids such as serum, plasma, synovial fluid, and ascitic fluid. In certain embodiments, various forms of enzyme-linked immunosorbent assay (ELISA) may be utilized in the assay.

Figure 2:
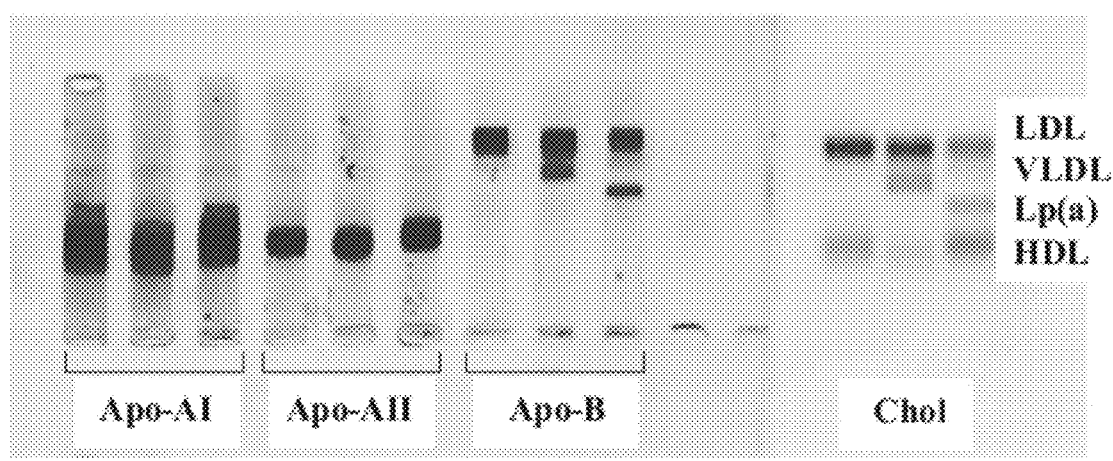
FIG. 2 depicts a gel probed for the presence of Apo-AI, Apo-AII, and Apo-B and stained for the presence of lipoprotein particles.
Figure 3:
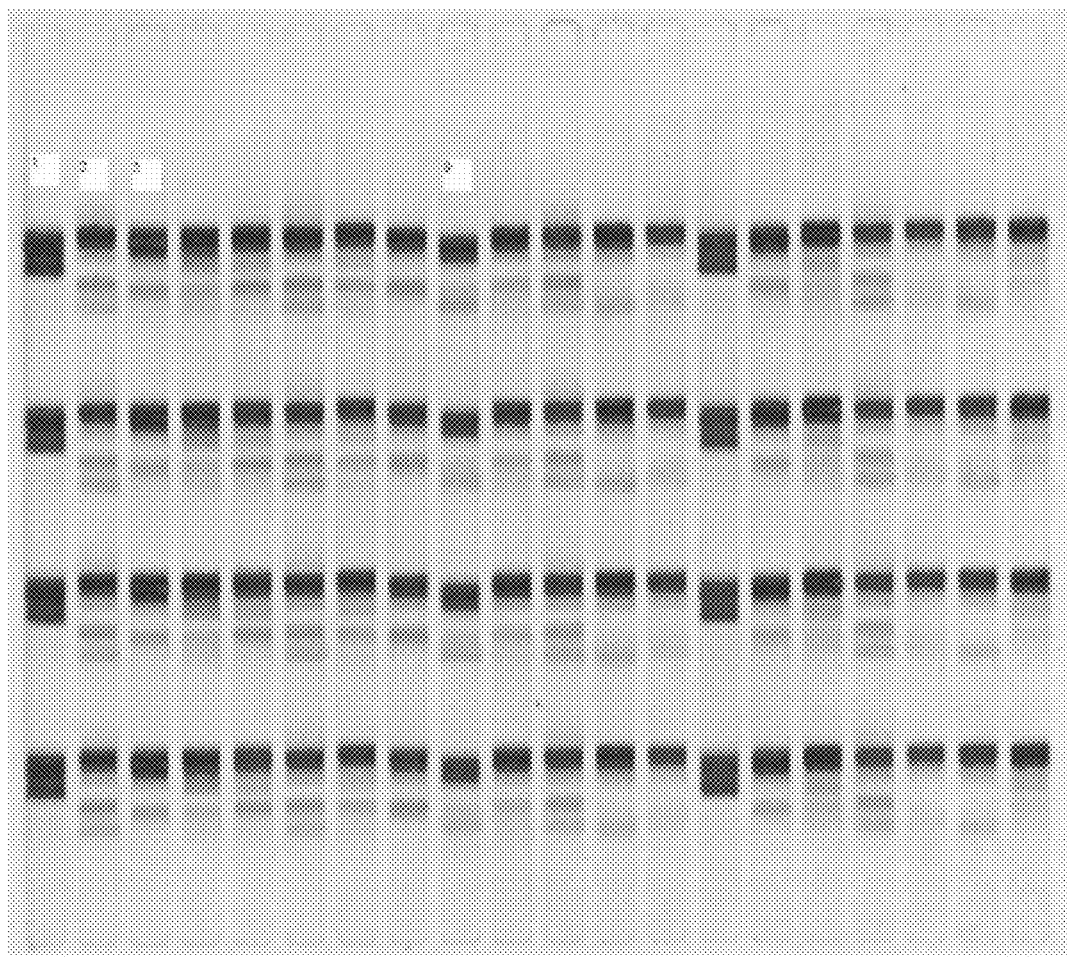
FIG. 3 depicts a gel containing samples from multiple patients, probed for the presence of Apo-B and stained for the presence of lipoprotein particles. The labels present on the lanes indicate the patient number.
Figure 4:
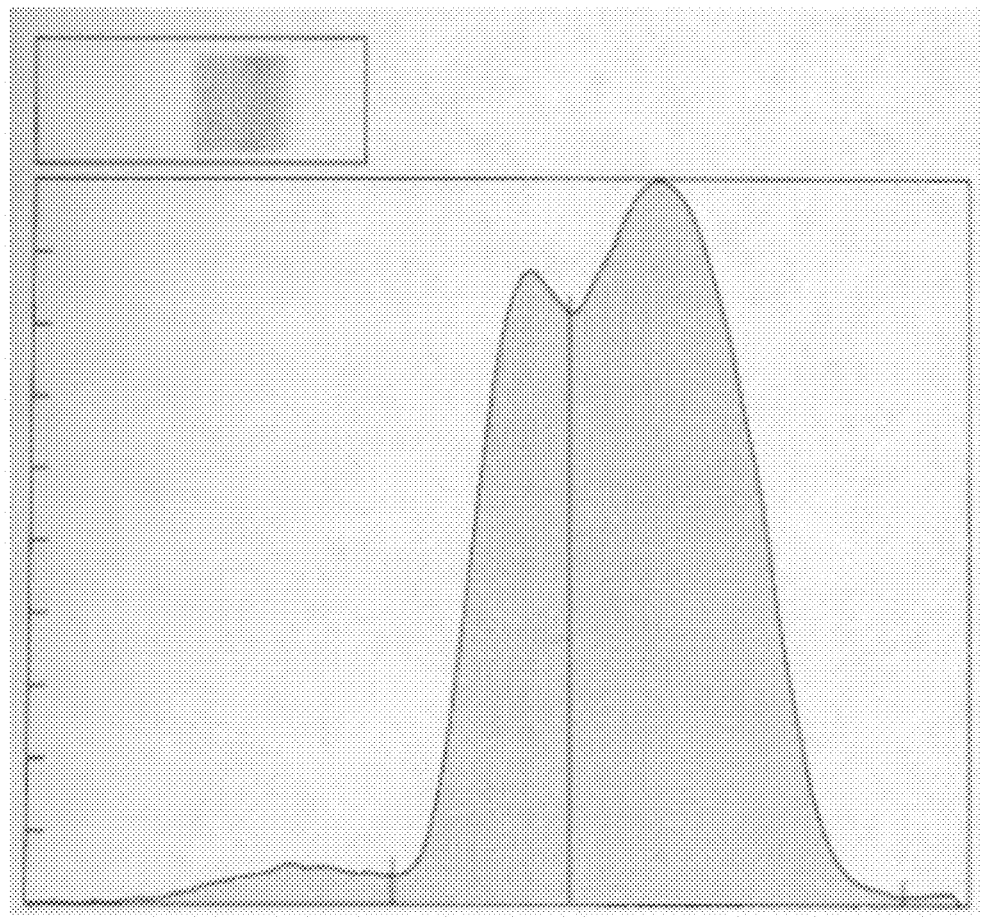
FIG. 4 depicts a densitometric scan of the bands present in the lane for patient 1 (labeled 1) in the gel depicted in FIG. 3. The fraction values represent the percentage of the peak area.
Figure 5:
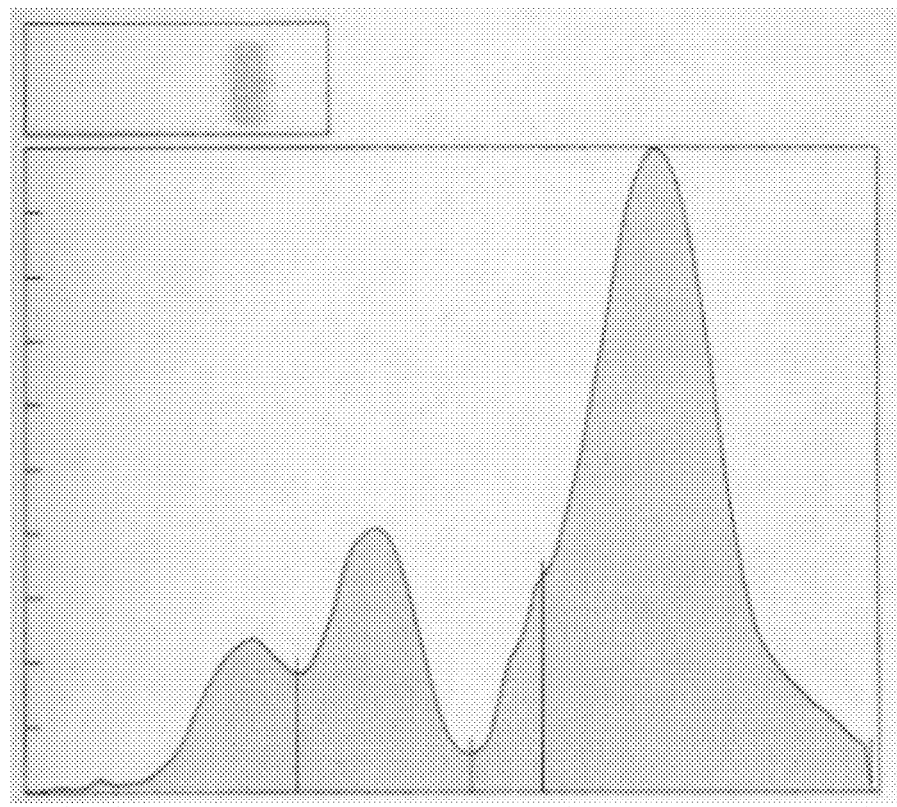
FIG. 5 depicts a densitometric scan of the bands present in the lane for patient 2 (labeled 2) in the gel depicted in FIG. 3. The fraction values represent the percentage of the peak area. (Fraction Labels: Lp(a)-P1, Lp(a)-P2, VLDL-P, LDL-P)
Figure 6:
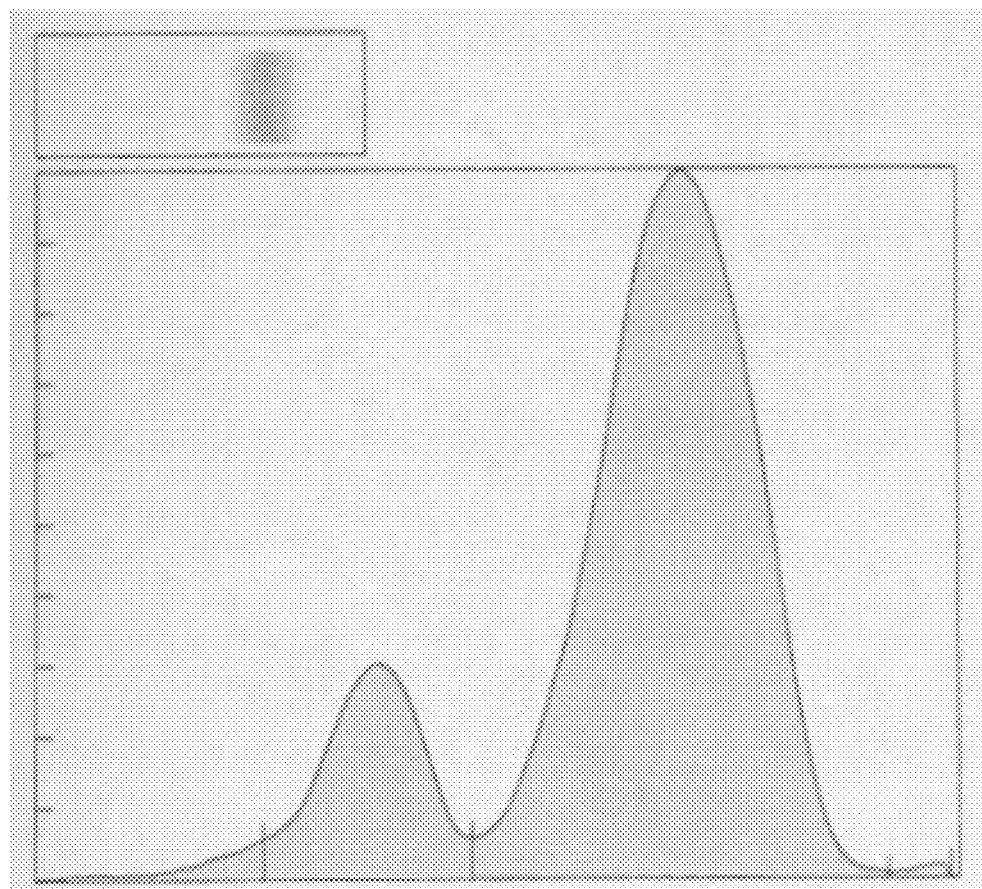
FIG. 6 depicts a densitometric scan of the bands present in the lane for patient 10 (labeled 10) in the gel depicted, in FIG. 3. The fraction values represent the percentage of the peak area. (Fraction Labels: Lp(a)-P1, Lp(a)-P2, LDL-P)
Figure 7:
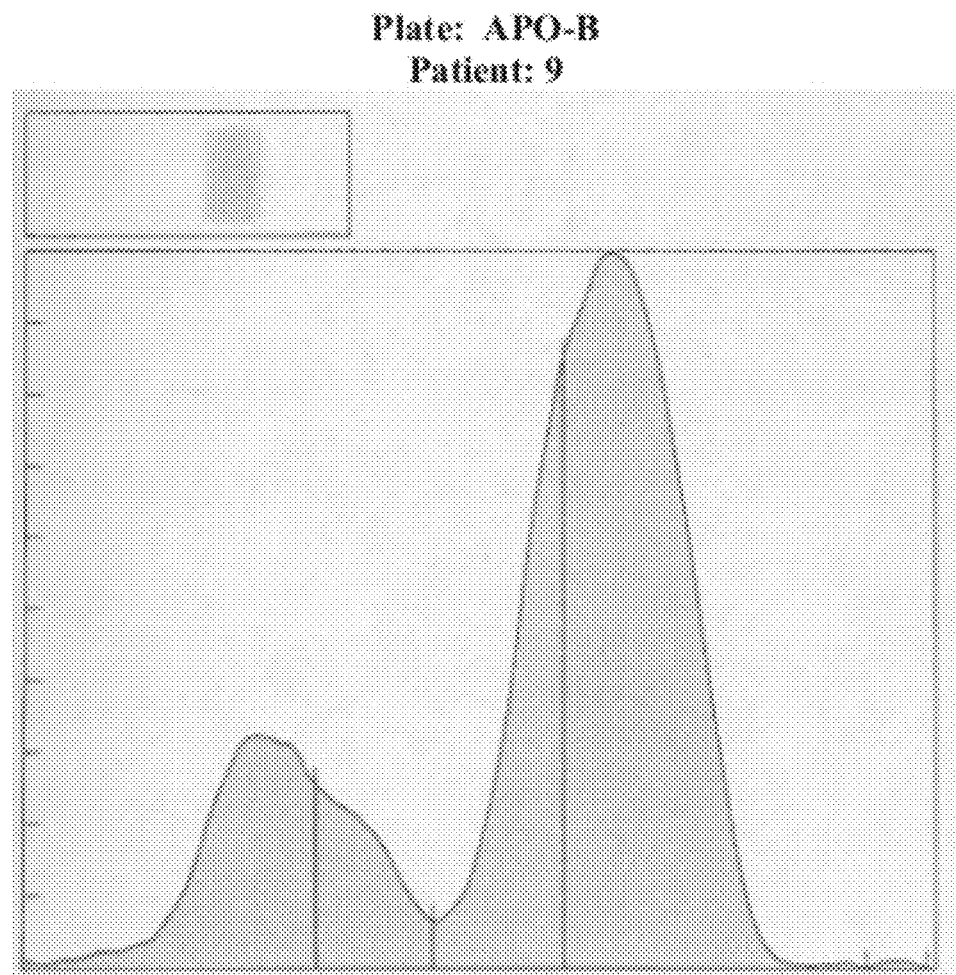
FIG. 7 depicts a densitometric scan of the bands present in the lane for patient 12 (labeled 12) in the gel depicted in FIG. 3. The fraction values represent the percentage of the peak area. (Fraction Labels: Lp(a)-P1, Lp(a)-P2, VLDL-P, LDL-P)

Referring to FIG. 2, lipoprotein particles were separated on a gel probed for Apo-AI, Apo-AII, and Apo-B and stained. FIG. 3 depicts a gel containing samples from multiple patients and probed for the presence of Apo-B. The labels present on the lanes indicate the patient number. FIGS. 4-8 depict the densitometic scans of the bands present in the lanes for various patient samples in FIG. 3. The fraction values represent the percentage of the peak area. FIG. 4 depicts a densitometric scan of the lane for patient 1 (labeled 1). FIG. 5 depicts a densitometric scan of the lane for patient 2 (labeled 2). FIG. 6 depicts a densitometric scan of the lane for patient 10 (labeled 10). FIG. 7 depicts a densitometric scan of the lane for patient 12 (labeled 12). FIG. 8 depicts a densitometric scan of the lane for patient 74 (labeled 74).

Ultracentrifugation separates lipoprotein particles based upon their densities. In an embodiment, a discontinuous NaCl/sucrose gradient may be used for separation by ultracentrifugation. In an embodiment, bodily fluids such as serum, plasma, synovial fluid, and ascitic fluid may be prestained with Fat Red 7B to visualize the bands for the lipids or acid violet to visualize the protein. Fractions may be isolated by bottom puncture of the tube. In one embodiment, fractions of individual lipoprotein particles may be probed for the amount of a given apolipoprotein.

Lipoprotein particles may be separated by various methods. In an embodiment, lipoprotein particles may be separated by column chromatography. In one embodiment the column chromatography may be performed on an HPLC. HPLC fractions may be collected and probed for the presence of a given apolipoprotein. In an embodiment, separation may be achieved by ELISA or precipitation. Alternatively, any suitable type of separation protocol known in the art may be used.

In one embodiment, densitometry is used to quantitate the levels of lipoprotein particles and apolipoproteins. The optical density of the bands is determined by exposing the bands to light and measuring the decrease in the amount of light that travels through the transparent gel. Other methods may be used to quantitate the amount of lipoprotein particles and apolipoprotein present in the bands. A processor may be attached to the densitometer to determine and analyze the optical density of the band for each lipoprotein particle and apolipoprotein. The values determined by the densitometer may be given as a ratio between the actual value and the positive control. The use of densitometry in quantifying bands is well known in the art. See U.S. Pat. Nos. 4,572,671; and 7,682,795.

In an embodiment, an apolipoprotein will be detected by precipitation upon binding of the apolipoprotein and the polyclonal antibody directed to it. In an embodiment, the presence or absence of a lipoprotein particles or apolipoprotein may be detected visually. In another embodiment, a protein stain may be utilized to detect the binding of the apolipoprotein and antibody. In an embodiment, a secondary antibody with a label may be utilized to detect the binding of the apolipoprotein and antibody.

The risk of development of a particular disease may be determined based upon a ratio of one component to another or based upon the actual levels of the components. Different methods of separation or detection may lend themselves to the use of ratios or actual levels. For instance, ratios may be preferred to detect risk if gel electrophoresis was used or actual levels may be preferred if ELISA was used. However, either may be used for any method of detection.

After possible lipoprotein particle and/or apolipoprotein targets are identified as being possible risk indicators for a disease, various combinations will be researched to determine which combinations are the best indicator. For instance, the level of a lipoprotein particle may be a good indicator of risk for a particular disease but analyzing the level of an additional component may improve the ability to predict an individual's risk of developing that disease. The levels of the target lipoprotein particles and apolipoproteins in a large collection of samples will be analyzed and compared to the disease data available for those samples to determine which are the best indicators of risk for a particular disease. In an embodiment, a diagnostic assay may be prepared using this information.

Assays to Determine Risk of Cardiovascular Disease

LDL deposits LDL cholesterol on the arterial wall which contributes to cardiovascular disease. Inflammation occurs when cholesterol builds up inside an artery wall. Macrophages appear because of the inflammation. The macrophages become foam cells when they take up LDL, causing additional inflammation. Inflammation indicates risk of cardiovascular disease.

An embodiment of the present disclosure determines how much Apo B is present from various lipoprotein particle sources, independent of plasma Apo B interference. This assay makes assessment of the atherogenicity of individual lipoprotein particles and apolipoproteins possible. These measurements provide an assay for determination of the risk of an individual for developing cardiovascular disease and provide a way to monitor treatment. High levels of Apo B and LDL particles indicate an increased risk for cardiovascular disease. In an embodiment, the method provides a method for the assessment of the number specific lipoprotein particles. The method allows for simultaneous, modifiable, charge/sized lipoprotein particle separations to be probed immunologically for various apolipoproteins. The method provides a direct measurement of lipoprotein particles. The method also provides a mechanism to determine which levels of specific lipoprotein particles are indicative of an increased risk for a given disease.

In an embodiment of the present disclosure, immunospecificity and simultaneous charge separation potential are combined to determine the level of specific lipoprotein particles. There is a 1:1 stoichiometry of the Apo B content for each of the lipoprotein particle types of which it is a component. Separation of serum lipoprotein particles, such as by gel electrophoresis, provide fractionation of Apo B. The method of detection of provides clinical information that may be utilized to develop a simple, easy-to-use, and quick diagnostic assay that detects the lipoprotein particle of interest for a specific disease. Other methods of separation known in the art may be used in place or in addition to gel electrophoresis. This assay detects lipoprotein particles with a protein or lipid stain and apolipoproteins with an antibody. FIG. 2. Other methods of detection know in the art may be used. The gels contents may be transferred to membrane such as nitrocellulose. Gels or membranes may be exposed to stain or antibody by incubation in a wash containing the reagent, exposing the gel or membrane to a film containing the reagent, or other method known in the art. In one embodiment, the gel is stained with Acid Violet. In one embodiment, the gel is stained with Oil Red O. In an embodiment, films containing the reagent or reagents should be clear, rapidly dissolving, supported, and complementary to the sensitivity required for the system. Different reagents may be present on the film at different locations corresponding to a particular lane on a gel to be probed. In another embodiment, liquid reagents were used. The optical density of each band may be determined by densitometry. The optical density may be correlated using a processor, such as a computer, calculated by hand, or by any other method known in the art.

An antibody to apolipoprotein B recognizes two bands in the area of where Lp(a) migrates. One band previously co-migrated with HDL and was detected using the method of simultaneous lipoprotein particle separation and immunological detection as disclosed herein. The slower migrating band is atherogenic. Therefore, a high level of that band indicates a higher risk for cardiovascular disease. Lipoprotein particles present in bodily fluids such as serum, plasma, synovial fluid, and ascitic fluid may be separated and exposed to reagents that detect lipoprotein particles and apolipoproteins. Apo B-100 is present as part of Lp(a) so probing with an Apo B-100 antibody will detect Lp(a). An example of a suitable protein stain is Acid Violet and a suitable lipid stain is Oil Red O. Any other suitable stains known in the art may be used.

Assays to Determine Risk of Late Onset Alzheimer's Disease

Apo E has been associated with the risk of late onset Alzheimer's Disease. Three different alleles of the Apo E gene exist, Apo E e2, e3, or e4. The alleles differ from each other by one or two base pairs. The presence of Apo E e4 correlates with an increased risk of late onset Alzheimer's Disease. Each person has a pair of Apo E genes that are a combination of e2, e3, and e4. Apo E e3/e3 is the most common genotype. Apo E e4/e4 and e4/e3 indicate a risk for atherosclerosis. Apo E e4 is also associated with an increased risk of late onset Alzheimer's disease, with e4/e4 being at the highest risk. An advantage of the present systems, methods, apparatus, and assemblies is the capability of detecting which Apo E proteins are present with which lipoprotein particles and at what levels. Antisera specific to Apo E e2, e3, or e4 will be used to determine which is present. Measuring total Apo E is not sufficient because it does not provide information on which lipoprotein particle the Apo E is present.

EXAMPLES

The following examples are included to demonstrate preferred embodiments of the present disclosure. Those of skill in the art should, in light of the present disclosure, appreciate that many changes can be made in the specific embodiments which are disclosed and still obtain a like or similar result without departing from the spirit or scope of the disclosure. The following Examples are offered by way of illustration and not by way of limitation.

Example 1

Preparation of Antibodies to Apolipoproteins

Polyclonal antibodies to an apolipoprotein will be produced by injecting a suitable animal host, such as a rabbit, with the apolipoprotein of interest and an adjuvant. Approximately 0.02 milliliters will be injected and reinjection occurs every 21 days until peak antibody titer is achieved. Antibody titer will be tested by an ear bleed. Antibodies to Apo B-100 or other apolipoprotein can be produced in this manner. Alternatively, antibodies to Apo B-100 or other apolipoprotein may be purchased commercially.

Example 2

Apo-B Procedure

A SPIFE Electrophoresis System by Helena Laboratories Corporation was used to analyze serum samples from various patients. Deep well disposable cup strips were placed into rows 2, 3, 4 and 5 of the sample cup tray. The blades were placed into the vertical slots numbered A, 9, 13 and 16 of the applicator assembly. 50 microliters of a patient sample or control was pipetted into the appropriate sample cups. In other embodiments, different volumes of patient samples may be used. In one embodiment, 75 microliters of a patient sample or control was pipetted into the appropriate sample cups.

Approximately 2 milliliters of REP Prep from Helena Laboratories Corporation was dispensed onto the left side of the electrophoresis chamber. REP is a coined term for Rapid ElectoPhoresis. The gel was placed on the REP Prep and a lint-free tissue was used to wipe around the edges of the gel backing to remove excess REP Prep. Special attention was taken to wipe next to the electrode posts. The protective gel overlay was removed from the gel and discarded. A Blotter C was used to gently blot the entire surface of the gel using slight fingertip pressure on the blotter. The blotter was then removed.

A carbon electrode was placed on the outside ledge of the cathode gel block (left) outside the magnetic posts. A stainless steel electrode was placed on the outside ledge of the anode gel block (right) outside the magnetic posts. An electrode blotter was placed under the ends of the carbon electrode so that they touched the gel block ends. The running parameters for electrophoresis were as follows:

samples were loaded in 30 seconds, samples were applied in 60 seconds, and electrophoresed for 20 minutes at 16° C. and 400 volts.

The electrodes were removed following electrophoresis and the gel blocks were removed and discarded. Apo-B antiserum was diluted 1:4 with saline (1 part antiserum with 3 parts saline). In other embodiments, a different concentration of antiserum may be used. The antisera template was gently placed onto the surface of the gel. 250 microliters of the diluted antiserum was pipetted into the oval slots at the right end of each antisera channel in the template. The antiserum was allowed to absorb for 10 minutes at 20° C.

After absorption was complete, one comb blotter was placed into the slots on the right end of the antisera channels such that the tips of the comb touched the gel. The antisera template and comb blotter was removed after 3 minutes. The surface of the gel was blotted with a Blotter C and the Blotter C was then removed and discarded.

Two Blotter Cs were wet in normal saline and placed on the gel surface. Four Blotter Ds were placed on top of the wet Blotter Cs. The antisera template was placed on top and blotted for 2 minutes. The antisera template and blotters were removed and discarded. Two Blotter Cs were wet and placed on the gel, four Blotter Ds were placed on the Blotter Cs, and the antisera template was placed on top and blotted for another 2 minutes.

An electrode was placed at each end of the gel, against the magnetic posts, to ensure good contact of the gel with the floor during drying. The gel was dried at 50° C. for 8 minutes.

The gel was removed from the electrophoresis chamber and attached to the gel holder of the Stainer Unit with the gel facing the back of the unit. The gel holder and gel were placed into the Stainer Unit. The gel was washed in TBS for 10 minutes, stained in Acid Violet stain for 4 minutes, destained twice in Citric Acid Destain for 1 minute each time, and dried at 63° C. for 8 minutes. The gel was then destained in Citric Acid Destain for 1 minute and dried at 63° C. for 5 minutes.

Example 3

Determining the Risk of Developing Cardiovascular Disease Using Apo B and LDL Levels Serum will be drawn from an individual to be tested for the risk of cardiovascular disease. Gel electrophoresis will be performed on the serum. The lipoprotein particles migrate based on their size/charge. One part of the gel will be developed with Fat Red 7B to detect lipids. Cholesterol will be detected with any cholesterol reagent known in the art. In one embodiment, the cholesterol reagent is formazan. Another part of the gel will be developed with a polyclonal antibody to Apo B-100 using immunofixation. Precipitation occurs when the antibody binds its antigen, Apo B-100. In an embodiment, the binding of an antibody and its antigen may be detected by using an antibody that is labeled or using a labeled secondary antibody.

Densitometry will be performed upon the bands for various specific lipoprotein particles. Densitometry will also be performed on the bands recognized by the antibody to Apo B-100. The matrix or medium was stained with Acid Violet following detection by the antibody. A high level of Apo B-100 and LDL particles correlates to an increased risk of cardiovascular disease. The present method also provides a method for specific lipoprotein particles in addition to a method for lipoprotein particle cholesterol levels and lipoprotein triglyceride levels.

Example 4

Determining the Risk of Developing Cardiovascular Disease Using Lp(a)-P Levels

One part of the gel will be developed with Acid Violet to detect proteins or Fat Red 7B to detect lipids. The gel will also be developed with a polyclonal antibody to Apo B-100. In an embodiment, the binding of an antibody and its antigen may be detected by using an antibody that is labeled or using a labeled secondary antibody. An antibody to apolipoprotein B recognizes two bands in the area of where Lp(a) migrates. The same antibody will recognize Apo-B in all lipoprotein particles containing Apolipoprotein-B, not only the Lp(a) "pair". One band previously co-migrated with HDL and was detected using the method of simultaneous lipoprotein particle separation and immunological detection as disclosed herein. If desired, cholesterol will be detected with any cholesterol reagent known in the art. In one embodiment, the cholesterol reagent will be formazan.

Densitometry will be performed upon the bands for various lipoprotein particles detected using Fat Red 7B, Acid Violet, a cholesterol agent, and the Apo B-100 antibody, (Densitometry cannot be used on the Apo-B antibody without suitable visualization protocols . . . there is no visibly optically active color intrinsic to the antigen-antibody binding without an appropriate detectable ligand or conjugate), to determine the level of lipoprotein particles. An increased level of lipoprotein particles containing Lp(a) indicates increased risk of cardiovascular disease.

Example 5

Determining the Risk of Developing Late Onset Alzheimer's Disease Using Apo E Levels Serum will be drawn from an individual to be tested for the risk of developing late onset Alzheimer's Disease. Gel electrophoresis will be performed on the serum. The lipoprotein particles migrate based on their size/charge. The gel will be developed with Acid Violet or Fat Red 7B lipoprotein particles. Cholesterol may be detected with any cholesterol reagent known in the art. In one embodiment, the cholesterol reagent will be formazan. Another portion of the gel will be developed with polyclonal antibodies to the e2, e3, and e4 alleles. In an embodiment, the binding of an antibody and its antigen may be detected by using an antibody that is labeled or using a labeled secondary antibody.

Densitometry will be performed upon the bands for various lipoprotein particles detected using Acid Violet. Densitometry may also be performed on the bands recognized by the antibody to e2, e3, and e4. Developing antisera probed complexes requires a suitable protein/lipid stain and/or visually active conjugate or ligand. The presence of e4 alleles correlate to an increased risk of cardiovascular disease, especially if an individual possesses two e4 alleles.

Example 6

Testing of Multiple Serum Samples

Gel electrophoresis has been performed using a large number of lanes (e.g. 80) of serum samples. FIG. 3. The serum samples were probed for Apo B. Each lane represents a patient sample. The densitometric tracings of the bands in the lanes for patients 1, 2, 3 and 9 are depicted in FIGS. 4-7 respectively.

Example 7

Diagnostic Assay

A diagnostic assay, to detect presence and/or levels of specific lipoprotein particles in bodily fluids, such as serum for the purpose of identifying risk of a particular disease, utilizes, in general terms, an electrophoretic support or platform, a "membrane" or reagent-containing film, and a densitometer, or the equivalent of one or more of the above. The membrane may provide the dual functions of a support during electrophoresis and may contain the reagent. The "membrane" or "reagent-containing film" may contain the antibodies. Antibodies to apolipoprotein A, apolipoprotein B, apolipoprotein C, apolipoprotein D, apolipoprotein E, or apolipoprotein H will be present in a spot in one lane on a membrane. Antibodies to high density lipoprotein particle, intermediate density lipoprotein particle, low density lipoprotein particle, very low density lipoprotein particle, or lipoprotein(a) particle, will be present in a spot in another lane on the membrane. The membrane will be blocked to prevent nonspecific binding of the antigen to the membrane. The assay will be provided to a user after which time the membrane will be incubated with a sample of serum to be tested for a given disease, such as cardiovascular disease. The antigens in the serum will bind to the antibodies present on the membrane. Unbound antigen will be washed off of the membrane. The membrane will then be incubated with a dye or antibody specific for the antigen and containing a detectable label. A band will be visible on the membrane where the antibody binds its antigen. A densitometer will be used to determine the amount of antigen present in the serum.

Variations and modifications to the preferred embodiments described herein will be apparent to those skilled in the art. It is intended that such variations and modifications may be made without departing from the scope and without diminishing its attendant advantages. The term densitometry conventionally relates to visually detectable/measurable color changes. However, any emitted spectral electromagnetic radiation linked to the analyte of interest with a complementary detector can "densitomize" the lipoprotein particles.

All of the compositions and methods disclosed and claimed herein can be made and executed without undue experimentation in light of the present disclosure. While the compositions and methods disclosed herein have been described in terms of preferred embodiments, it will be apparent to those of skill in the art that variations may be applied to the compositions and methods and in the steps or in the sequence of steps of the methods described herein without departing from the concept, spirit and scope. More specifically, it will be apparent that certain agents which are both chemically and physiologically related may be substituted for the agents described herein while the same or similar results would be achieved. All such similar substitutes and modifications apparent to those skilled in the art are deemed to be within the concept, spirit, and scope as defined by the appended claims. Further, all published documents, patents, and applications mentioned herein are hereby incorporated by reference, as if presented in their entirety.

What is claimed is:

1. A method of assessing the level of specific lipoprotein particles present in a bodily fluid comprising, in sequential order:
   (a) separating lipoprotein particles present in a bodily fluid sample by electrophoresis on a single gel substrate, wherein the lipoprotein particles have not been subjected to pre-separation from one another prior to said separating of step (a);
   (b) exposing the gel substrate to a first reagent, wherein the first reagent is an anti-apoB antibody, to form a lipoprotein/antibody complex, wherein said exposing causes aggregation and/or precipitation of the lipoprotein/antibody complex, thereby fixing the complex in the gel substrate without disturbing the gel; said first reagent not denaturing the lipoprotein;
   (c) exposing the gel substrate to a second reagent for detection of the presence of said specific lipoprotein particles, wherein the second reagent is a protein stain;
   (d) detecting within the gel substrate the specific lipoprotein particles based on said exposing steps (b) and (c); and
   (e) quantitatively assessing, based on said detection of (d), the level of the specific lipoprotein particles.

2. The method of claim 1, wherein step (d) comprises determining an optical density of a signal on the substrate indicating the level of a specific lipoprotein particle.

3. The method of claim 1, wherein step (d) comprises visually detecting a signal on the substrate indicating the level of a specific lipoprotein particle.

4. The method of claim 1, wherein the protein stain is Acid Violet.

* * * * *